United States Patent [19]

Fleck

[11] 4,386,200
[45] May 31, 1983

[54] 7-STYRYL COUMARIN DERIVATIVES

[75] Inventor: Fritz Fleck, Bottmingen, Switzerland

[73] Assignee: Sandoz Ltd., Basel, Switzerland

[21] Appl. No.: 306,966

[22] Filed: Sep. 30, 1981

[30] Foreign Application Priority Data

Oct. 3, 1980 [CH] Switzerland ............... 7404/80
Oct. 3, 1980 [CH] Switzerland ............... 7405/80

[51] Int. Cl.³ .................................... C09B 23/10
[52] U.S. Cl. ............................ 542/441; 549/220; 549/280; 548/220; 548/256
[58] Field of Search ......................... 542/441

[56] References Cited

U.S. PATENT DOCUMENTS 4,299,894 11/1981 Klose et al. ............... 542/441

OTHER PUBLICATIONS

Arch. Pharmaz. (305), 1972, pp. 124–134.

Primary Examiner—Jane T. Fan
Attorney, Agent, or Firm—Gerald D. Sharkin; Richard E. Vila; Thomas C. Doyle

[57] ABSTRACT

A non-chromophoric conjugated derivative of 7-styryl coumarin for use as an optical brightener in which the lactone ring of the coumarinyl group may have a benzene ring fused to it to form a 3,4-benzocoumarinyl-7 group, the phenyl group of the styryl is substituted by a conjugated group which contains a group derived from an acid in its conjugation and which group is so located as to conjugate with the ethylene group.

9 Claims, No Drawings

7-STYRYL COUMARIN DERIVATIVES

The invention relates to conjugated derivatives of 7-styryl coumarin, for use as optical brighteners and processes for preparing and using these derivatives.

In this specification the term "conjugated group" is used to cover groups having at least two double bonds or one double bond and one triple bond or an aromatic ring containing system. The term "styryl" is used in this specification to include groups in which the phenyl ring of the styryl has at least one five or six membered cyclic group fused in the 3,4-position (with respect to the attachment of the vinyl group to the phenyl).

To avoid doubt the coumarinyl-7 group is numbered as shown below

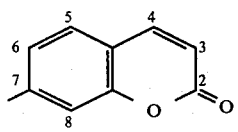

The invention provides a non-chromophoric conjugated derivative of 7-styryl coumarin in which the lactone ring of the coumarinyl group may have a benzene ring fused to it to form a 3,4-benzocoumarinyl-7 group but may have no other electron accepting or ionic group attached;

the phenyl group of the styryl is substituted by a conjugated group which contains a group derived from a carboxylic or sulphonic acid in its conjugation and which group is so located on the phenyl ring as to conjugate with the ethylene group and the phenyl group may be substituted by a further non-chromophoric group, and the conjugated derivative and the styryl group contain a maximum of three six-membered rings and one five membered ring where the five-membered ring may include up to two heteroatoms, with the proviso that the conjugated derivative and the styryl group do not form a coumarinyl-6 group.

Examples of electron-accepting groups excluded from the lactone ring of the coumarinyl-7 group are carboxylic acids or derivatives of carboxylic acids and unsaturated hydrocarbons (except for a benzene ring fused in the 3,4-position of the coumarinyl-7 group) that conjugate with the conjugation of the coumarinyl-7 group.

Examples of ionic groups excluded from the lactone ring are amino groups and hydroxy aromatic groups.

Preferably there are no electron-accepting or ionic groups on the coumarinyl-7 group in the remaining positions (i.e. 5-, 6- and 8-positions) of the coumarinyl-7 group.

In the conjugated group of the styryl preferably there are no ionic groups present other than an amide group. In particular no acid group and no aromatic hydroxy group is present.

Examples of groups derived from carboxylic or sulphonic acids that may be present in the conjugated group are esters, amides, sulphone, nitrile, lactone, lactam, oxazole and imidazole.

Preferably the conjugated group of the styryl (when it contains a ring), the coumarinyl-7 group and the phenyl group to which the conjugated group is attached may each, independently be substituted by one or more substituents, preferably one substituent, selected from alkyl, cycloalkyl, non-chromophoric and non-ionic aralkyl, alkoxy or halogen.

More preferably the phenyl group is further unsubstituted.

Any alkyl or alkoxy group referred to herein has 1 to 6 carbon atoms and may be a linear or branched alkyl or a cycloalkyl, more preferably linear or branched alkyl of up to 4 carbon atoms. Any alkyl is most preferably methyl, ethyl, isopropyl, isobutyl or tertiary butyl and any alkoxy is most preferably methoxy or ethoxy.

Any aralkyl referred to herein is preferably $C_{1-4}$alkyl substituted by phenyl which may in turn be substituted by a substituent selected from chlorine, methyl or methoxy.

Preferably the coumarinyl-7 group is of the formula (i)

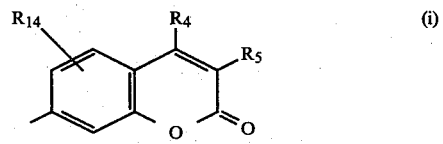

in which $R_4$ and $R_5$, independently, are hydrogen, $C_{1-4}$alkyl or $C_{1-4}$alkyl monosubstituted by phenyl which phenyl is unsubstituted or monosubstituted by methoxy, methyl or chlorine; or $R_4$ and $R_5$ together with the coumarinyl-7 group to which they are attached form a 3,4-benzocoumarinyl-7 group in which the 3,4-benzo group is substituted by two substituents $R_{20}$ selected from hydrogen, $C_{1-4}$alkyl, $C_{1-4}$alkoxy or chlorine; or $R_4$ and $R_5$ together with the coumarinyl-7 group to which they are attached form a 3,4-fused cyclo $C_{5-6}$alkenyl coumarinyl-7 group substituted by two substituents $R_{20}$ above defined; and $R_{14}$ is hydrogen, chlorine, $C_{1-4}$alkyl, or $C_{1-4}$alkyl substituted by phenyl which phenyl is unsubstituted or monosubstituted by methoxy, methyl or chlorine.

Preferably $R_{14}$ is $R_{14}'$ where $R_{14}'$ is hydrogen or chlorine; most preferably $R_{14}$ is hydrogen.

Preferably $R_{20}$ is hydrogen or $C_{1-4}$alkyl; more preferably $R_{20}$ is $R_{20}'$ where $R_{20}'$ is hydrogen, methyl, ethyl, isopropyl, isobutyl or tertiary butyl; most preferably $R_{20}$ is hydrogen.

Preferably $R_4$ and $R_5$ independently, are hydrogen or $C_{1-4}$alkyl or $R_4$ and $R_5$ together with the coumarinyl-7 group form a 3,4-benzo coumarinyl-7 group in which the 3,4-benzo group is substituted by up to two $R_{20}$ substituents.

More preferably $R_4$ is $R_4'$, where $R_4'$ is hydrogen, methyl, ethyl, isopropyl, isobutyl or tertiary butyl and $R_5$ is hydrogen or $R_4'$ and $R_5$ together with the coumarinyl-7 group to which they are attached form a 3,4-benzocoumarinyl-7 group substituted by up to two groups $R_{20}'$ defined above. When $R_5$ is hydrogen, $R_4'$ is preferably hydrogen, methyl or ethyl.

Most preferably $R_4$ is $R_4''$, where $R_4''$ is hydrogen or methyl and $R_5$ is hydrogen or $R_4''$ and $R_5$ together with the coumarinyl-7 group to which they are attached form an unsubstituted 3,4-benzo-coumarinyl-7 group.

Where the conjugated derivative of the styryl group is a 7-coumarinyl group this has the preferred significances as above but most preferably the conjugated derivative is identical with the coumarinyl-7 group.

The conjugated derivative of the styryl group is preferably a coumarinyl-7 group in which the lactone ring has no electron accepting or ionic groups bound thereto, a benzoxazolyl substituted by no ionic groups or a 4-vinyl group in which the β carbon atom of the vinyl group is substituted by a carboxylic acid ester, a carboxylic acid amide, a nitrile or a sulphone group.

Preferred significances of the conjugated group together with the phenyl group are

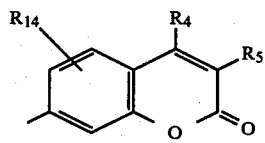
(ii)

where $R_4$, $R_5$ and $R_{14}$ are above defined; $R_{14}$ is preferably hydrogen;

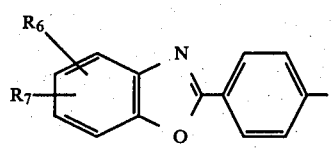
(iii)

where
$R_6$ and $R_7$ independently are hydrogen, $C_{1-4}$alkyl, halogen or $C_{1-4}$alkyl substituted by a phenyl group which is unsubstituted or monosubstituted by methyl, methoxy or chlorine, or $R_6$ and $R_7$ are ortho to each other and form a 5- or 6-membered cycloalkylene group which is fused to the phenyl ring to which $R_6$ and $R_7$ are attached;

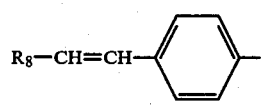
(iv)

where
$R_8$ is —CN, —COOR$_9$, CONR$_{10}$R$_{11}$ or SO$_2$R$_{12}$;

$R_9$ and $R_{12}$ independently are $C_{1-4}$alkyl, $C_{1-4}$-alkyl substituted by a phenyl group which is unsubstituted or monosubstituted by methyl, methoxy or chloro, $C_{2-4}$alkyl monosubstituted by hydroxy, $C_{1-4}$alkoxy or $C_{1-4}$alkoxy-$C_{2-6}$-alkoxy, cyclohexyl unsubstituted or substituted by up to three methyl groups or phenyl unsubstituted or monosubstituted by $C_{1-4}$-alkyl, trifluoromethyl, cyano, $C_{1-4}$alkoxy, chloro or carboxy;

$R_{10}$ is hydrogen, $C_{1-4}$alkyl, $C_{1-4}$alkyl substituted by phenyl which is unsubstituted or monosubstituted by methyl, methoxy or chloro, or $C_{2-4}$alkyl monosubstituted by hydroxy, $C_{1-4}$-alkoxy or $C_{1-4}$alkoxy-$C_{2-6}$alkoxy; and $R_{11}$ has the significances of $R_{10}$ (independently of $R_{10}$) and phenyl unsubstituted or substituted by $C_{1-4}$alkyl, trifluoromethyl, chloro, cyano, carboxy or $C_{1-4}$alkoxy.

Preferably $R_6$ and $R_7$ are in the 5- or 6-position of the benzoxazolyl group.

Preferably $R_6$ is hydrogen, chlorine or $C_{1-4}$alkyl; more preferably $R_6$ is $R_6'$, where $R_6'$ is hydrogen, chloro, methyl, ethyl, isopropyl, isobutyl or tertiary butyl and $R_7$ is hydrogen.

Preferably $R_8$ is $R_8'$, where $R_8'$ is —CN or COOR$_9'$ where $R_9'$ is $C_{1-4}$alkyl or $C_{2-3}$alkyl monosubstituted by methoxy or ethoxy.

Preferred compounds of the invention are of the formula I, $$R-CH=CH-R_1 \qquad I$$

in which
$R_1$ is a coumarinyl-7 or 3,4-benzocoumarinyl-7, the lactone ring of the coumarinyl-7 group having no electron accepting or ionic groups; and R is coumarinyl-7 or 3,4-benzocoumarinyl-7, the lactone ring of the coumarinyl-7 group having no electron accepting or ionic group present, or a benzoxazolyl phenyl group containing no ionic groups or a 4-vinyl-phenyl group in which the β carbon atom is substituted by a carboxylic acid ester, a carboxylic acid amide, a nitrile group or a sulpho group.

More preferred compounds of the invention are of the formula I'

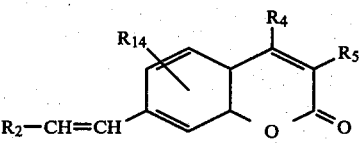
I' where
$R_2$ is one of the groups (ii), (iii) and (iv) above defined and
$R_{14}$, $R_4$ and $R_5$ are as defined above.

Preferred compounds of formula I' are of formula II

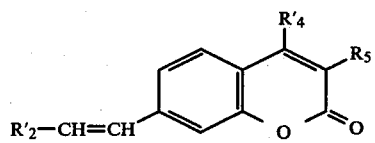
II in which
$R_4'$ is hydrogen, methyl, ethyl, isopropyl, isobutyl or tertiary butyl and $R_5$ is hydrogen; or $R_4'$ and $R_5$ together with the coumarinyl-7 group to which they are attached form a 3,4-benzocoumarinyl-7 substituted by up to two $R_{20}'$ groups as defined above; and $R_2'$ is one of the groups (ii), (iii) and (iv) defined above where in group (ii) $R_4$ and $R_5$ have the significances of $R_4'$ and hydrogen respectively or together with the coumarinyl-7 group to which they are attached form a 3,4-benzocoumarinyl-7 group where in group (iii) $R_6$ is $R_6'$ defined above and $R_7$ is hydrogen and where in group (iv) $R_8$ is defined above.

More preferred compounds of formula I' are of the formulae III

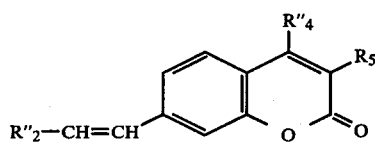
III in which $R_2''$ is a group of one of the formulae (iia) (iiia) and (iva)

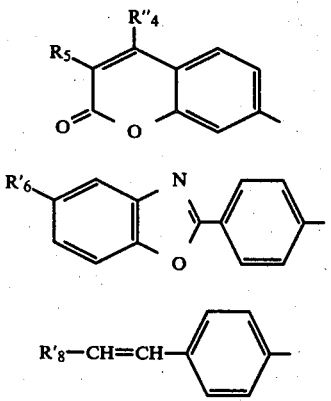 (iia)

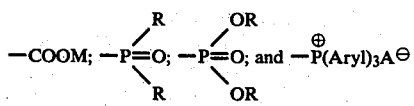

(iiia)

(iva)

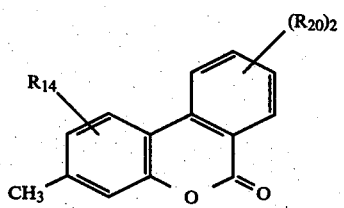

where
A$^\ominus$ is a non-chromophoric anion,
M is hydrogen or a colourless cation,
and R is alkyl, cycloalkyl or aryl.

Further according to the invention there is provided a compound of formula IV where $R_4''$, $R_5$, $R_6'$ and $R_8'$ are defined above.

Most preferred compounds of formula I' are of the formulae IIIa and IIIb below.

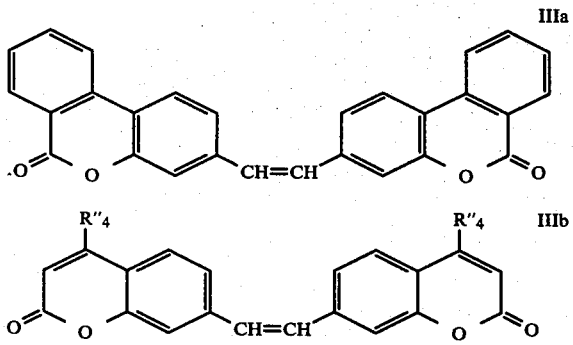

IIIa

IIIb where $R_4''$ is defined above, when $R_5$ is hydrogen.

Preferably the compounds of the invention are symmetrical.

The compounds of the invention can be prepared by reacting a compound of the formula $R_{30}$-X with a compound of the formula $R_{31}$-Y where $R_{30}$ is a styryl group the phenyl of which is substituted by a conjugated group which contains a group derived from a carboxylic acid or sulphonic acid in its conjugation and which group is so located on the phenyl ring as to conjugate with the ethylene group and the phenyl group may be substituted with a further non-chromophoric group and the conjugated group and the styryl group contain a maximum of three six-membered rings and one five-membered ring which five membered ring may include up to two hetero atoms, with the proviso that the conjugated derivative and the styryl group do not form a coumarinyl-6 group.

$R_{31}$ is a coumarinyl-7 group in which the lactone ring of the coumarinyl-7 group may have a benzene ring fused thereto to form a 3,4-benzocoumarinyl-7 group but may have no other electron accepting or ionic groups. One of X and Y is an aldehyde or a derivative thereof and the other of X and Y is —CH$_2$—Z where Z is hydrogen or a group activating the methylene group. Preferably $R_{30}$ is R as defined above and $R_{31}$ is $R_1$ as defined above.

A preferred derivative of aldehyde is an anil or an acetal.

Examples of the substituent Z are carboxylate or phosphonic acid ester groups or triarylphosphonium, in particular compounds of the formulae

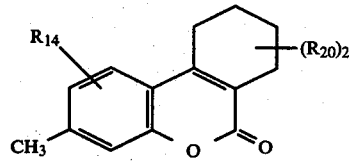

where $R_{20}$ is above defined, the dehydrogenating step being known.

The compounds of formula IV are useful as starting materials for preparing the 7-styryl-coumarin of the invention where the coumarinyl-7 group has a 3,4-benzo group fused thereto.

The compounds of formula V can be made from m-cresols and cyclohexanone carboxylic esters according to the Pechmann reaction.

The other starting materials $R_{30}$-X and $R_{31}$-Y are known or can be produced according to analogous known methods, for instance where appropriate from the corresponding compound of formula IV or from the corresponding 7-methyl coumarin.

Where a symbol appears more than once in a formula it may be the same or different.

The compounds of the invention absorb in the U.V. part of the spectrum and fluoresce in the violet-blue part of the spectrum. The compounds of the invention are useful as optical brighteners for natural, synthetic or mixed natural and synthetic textile material or for non-textile material. Preferably the compounds of the invention are useful as optical brighteners for synthetic or semi synthetic high molecular weight polymers such as polyester, polyamide, polyurethane, polyolefin (such as where
$R_{20}$ and $R_{14}$ are as above defined
$R_{20}$ has the same preferences as $R_{20}$ above;
and $R_{14}$ has the same preferances as $R_{14}$ above, most preferably being hydrogen.

The compounds of formula IV can be prepared according to analogous known methods for example according to Heacock and Hey (Journal of the Chemical Society 1954 2481-4) or by dehydrogenating a compound of formula V polypropylene) polyvinylchloride and cellulose esters, such as 2,5-diacetate and triacetate.

The brightened material preferably is in the form of fibre material, for example as thread, filament woven or knitted fabric or finished or half-finished material.

The optical brighteners of the invention can be applied to the substrate to be brightened by known methods for example by exhaust brightening or by impregnating (in particular dipping or padding) followed by a fixing step for example with saturated steam (preferably at temperatures of 95°–120° C.) or by high temperature treatment (for example 105° to 150° C.) or by a thermosol process.

The optical brightener of the invention can be applied to textile material in the form of an aqueous dispersion, which may, if desired, contain further assistants such as a carrier, dispersing agent or thickening agent.

Of the above methods of application, the most preferred is application with an aqueous bath, particularly with compounds of formula III when $R_2''$ is a group of formula IIIa or iva.

The compounds of the invention can be applied to plastics material (such as fibre-forming polymers) while in the mass (for example as an addition to a polymer melt or solution, to a monomer, prepolymer, or precondensate).

In brightening polyester fibres, preferably polyglycolterephthalate, in mass, the brightener can be used in powder form particularly when added to the mass or during polycondensation.

The compounds of the invention that are useful in a spinning mass are preferably compounds of formula III where $R_2''$ is a group of the formula iia or iiia, more preferably compounds of formula IIIa or IIIb. These latter compounds show a good stability.

The concentration of optical brightener used is variable for example between 0.001 to 0.5 preferably 0.01 to 0.1% with respect to the material to be brightened.

The optical brighteners of the invention have good stability to heat and good light fastness properties as well as having a high yield. The brighteners can be used singly or as a mixture or in combination with known brighteners which have nuances that will counter the nuance of the optical brighteners of the invention. It is possible for an optical brightener of the invention to be combined with another optical brightener, applicable in the same or similar way as that of the compound of the invention and which other brightener has a part of the molecule in the same series as that of the invention.

Preferably reddish to violet-blue fluorescing brighteners of the invention are combined with greenish to neutral blue optical brighteners. Various optical brighteners with which the brighteners of the invention can be combined are described in German Offenlegungsschrift 2602750 and French Patents 1358820, 1535813 and 2149952.

In the polyester spinning mass the compounds of the invention give a relatively red to violet nuance with a high maximum white. These are preferably mixed with optical brighteners with blueish nuances (for example those of French Pat. No. 1358820 and it is thereby possible to obtain a high maximum white effect.

Optical brightener preparations can be prepared with an optical brightener of formula I preferably comprising 10 to 90%, preferably 30 to 70% of a compound according to the invention and 90 to 10% preferably 70 to 30% of a compatible optical brightener of blueish or greenish nuance.

By the term a compatible optical brightener is meant an optical brightener which when mixed with an optical brightener of the invention brings the hue closer to white than the hue of the optical brightener of the invention alone.

In the following Examples all percentages and parts are by weight and all temperatures are in degrees Centigrade unless indicated to the contrary.

EXAMPLE 1

(a) A mixture of 214 parts of 3,4-cyclohexeno-7-methylcoumarin and 454 parts 2,3-dichloro-5,6-dicyano-1,4-benzoquinone is stirred in 6000 parts of dry dioxane for 18 hours at 105°.

The reaction mixture is cooled to 20° and filtered and the filtrate is vacuum dried. The dark residue is hot extracted in 5000 parts white spirit (a hydrocarbon mixture having a boiling point of 150°–190° C.) and the product, that crystallizes out when the solution is cooled, is recrystallized in alcohol. The product is 3,4-benzo-7-methylcoumarin, a compound of formula 1

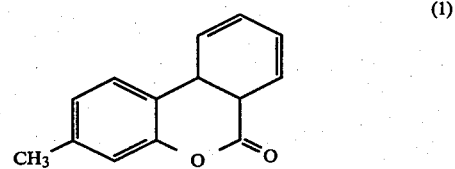

(1)

which melts at 130°–131° C.

(b) 210 Parts of the above product, 200 parts of N-bromosuccinimide and 2 parts of benzoyl peroxide is refluxed for 8 hours in 3000 parts of dry carbon tetrachloride. The reaction mixture when cold is filtered and the residue washed with water and vacuum dried. The product that results is 3,4-benzo-7-bromomethylcoumarin, a compound of formula 2

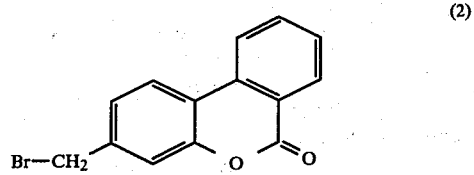

(2)

which melts at 180°–184° C. The yield is 90% of theory as white crystals.

(c) 156 Parts of the compound of formula 2 and 95 parts of hexamethylenetetraamine are refluxed in 700 parts of a 50% acetic acid solution for about 4 hours.

7-formylcoumarin, a compound of formula 3

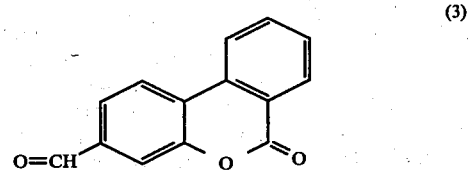

(3)

is formed and is suction-filtered and dried. The product melts at 271°–273°. The yield is 78% of theory and is in the form of light beige crystals.

(d) A mixture of 70.3 parts of the compound of formula 2 and 54 parts of triethylphosphite is refluxed using an oil bath, whilst gently stirring and ethyl bromide is distilled off.

The reaction solution is stirred for a further 2 hours at 150° (inner temperature) and excess triethylphosphite is distilled off under partial vacuum. The residue crystallizes out cold and is washed and dried under suction with a little petroleum ether (boiling point 70° C.). The resultant product is 3,4-benzo-7-(diethoxyphosphonomethyl)-coumarin, a compound of the formula 4.

(4)

C₂H₅O
 |
O=P—CH₂
 |
C₂H₅O which melts at 136°–138° C., is in the form of white crystals and has a yield of 95% theory.

(e) 173 Parts of the compound of formula 4 together with 112 parts of the compound of formula 3 is suspended in 1200 parts of dimethylformamide. Whilst stirring a solution of 13 parts sodium in 200 parts of absolute methanol is added dropwise and the yellow suspension is stirred a further 2 hours, and neutralized with acetic acid to a pH of 6 to 7. 200 parts of methanol is added and the resultant yellow precipitate is filtered by suction, washed with water and dried in a vacuum to give 162 parts of a compound of formula 5

(5)

which can be purified by recrystallizing from trichlorobenzene. The product melts over 340° and is in the form of fine greenish yellow needles.

Instead of using the compound of formula 4 a phosphonium salt formed from 145 parts of the bromo compound of formula 2 and 157 parts of triphenylphosphine may be used.

The optical brightener of formula 5 fluoresces, when dissolved in chlorobenzene, with a reddish violet hue and produces, particularly in polyethyleneterephthalate or polyamide (for example polycaprolactam) a strong brightening effect with a high maximum white of reddish hue and is capable of producing good fastness properties when applied to a substrate.

EXAMPLE 2

(a) According to the procedure of Example 1(b) 7-bromocoumarin a compound of formula 6

(6)

Br—CH₂ is produced from 7-methylcoumarin, N-bromosuccinimide and benzoyl peroxide.

(b) From the compound of formula 6 and hexamethylenetetramine, 7-formylcoumarin, a compound of formula 7

(7)

O=CH is produced according to the procedure of Example 1(c).

(c) 34.6 Parts of the compound of formula 4 and 17 parts of the compound of formula 7 is suspended in 500 parts of dimethylformamide. 2.6 Parts of sodium in 25 parts of absolute ethanol is added dropwise to the suspension whilst stirring and the mixture is stirred for a further hour at 40°–50° C.

(d) The mixture is then neutralized with acetic acid to a pH of 6–7 and then thinned with 500 parts of ethyl alcohol. A compound of the formula 8

(8)

CH=CH useful as an optical brightener, crystallizes out, is suction filtered at room temperature, washed and dried. The yield is 81% of theory, after recrystallisation in trichlorobenzene melts at 306°–307° C. and is in the form of lemon-yellow flakes.

Instead of using triethylphosphite, trimethylphosphite may be used and instead of sodium ethylate sodium hydride or potassium t-butylate may be used.

The compound of formula 8 fluoresces in chlorobenzene with a reddish blue hue and can be used as a synthetic fibre brightener for example in a spinning or padding procedure.

EXAMPLE 3

(a) A compound of formula 9

(9)

CH₃

O=CH is produced according to the procedure of Example 1(c) from 7-bromomethyl-4-methylcoumarin. The yield is 69% of theory and the product melts at 195°–197° C.

(b) A compound of formula 10

(10)

CH₃

CH=CH is produced according to the procedure of Example 2(c) from the compound of formula 4 (defined in Example 1), and the compound of formula 9 in N-methylpyrrolidone at 0°–5° C., adding the sodium in ethanol slowly and stirring the mixture for 2 hours at 10° C.

The compound of formula 10 has a yield of 80% of theory which, after recrystallising in trichlorobenzene melts at 305°–306° C. and is in the form of fine yellow prisms.

EXAMPLES 4 TO 9

Starting with suitable reagents and following the procedure of Example 1 compounds of the formula

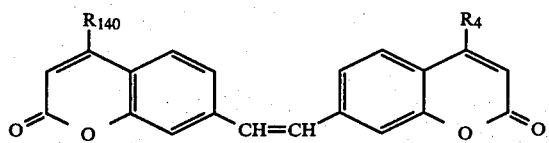

can be produced in which R₄ and R₁₄ are defined in Table 1 below.

TABLE 1

| Example No. | R₄ | R₁₄₀ | hue of the fluorescence in chlorobenzene |
| --- | --- | --- | --- |
| 4 | —CH₃ | —CH₃ | reddish violet |
| 5 | —CH₃ | —H | — |
| 6 | —H | —H | reddish blue |
| 7 | —C₂H₅ | C₂H₅ | violet blue |
| 8 | —CH(CH₃)₂ | —CH(CH₃)₂ | violet blue |
| 9 | —C(CH₃)₃ | —C(CH₃)₃ | reddish blue |

EXAMPLES 10 TO 21

Starting with suitable reagents and following the procedure of Example 1 compounds of the formula

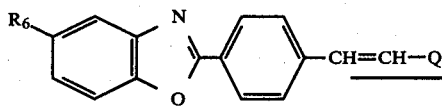

may be produced, in which R₆ and Q are defined in Table 2 below.

TABLE 2

| Ex. No. | R₆ | Q | melting point | Hue of the fluorescence in chlorobenzene |
| --- | --- | --- | --- | --- |
| 10 | —H | 3,4-benzocoumarinyl-7 | 280–281 | violet-blue to neutral-blue |
| 11 | —CH₃ | 3,4-benzocoumarinyl-7 | 301–305 | violet-blue |
| 12 | —Cl | 3,4-benzocoumarinyl-7 | 314–315 | violet-blue |
| 13 | —C(CH₃)₃ | 3,4-benzocoumarinyl-7 | 271–272 | blue |
| 14 | —H | coumarinyl-7 | 272–273 | violet-blue to blue |
| 15 | —CH₃ | coumarinyl-7 | 283–284 | greenish-blue |
| 16 | —Cl | coumarinyl-7 | 293–294 | violet-blue |
| 17 | —C(CH₃)₃ | coumarinyl-7 | 276–277 | greenish-blue |
| 18 | —H | 4-methylcoumarinyl-7 | 296–299 | violet-blue |
| 19 | —CH₃ | 4-methylcoumarinyl-7 | 293–294 | violet-blue |
| 20 | —Cl | 4-methylcoumarinyl-7 | 316–317 | violet-blue |
| 21 | —C(CH₃)₃ | 4-methylcoumarinyl-7 | 237–238 | blue |

These compounds are useful as optical brighteners for polyester, polyamide, polyolefin, cellulose-2,5-diacetate and triacetate, and polyvinylchloride, preferably for polyester, polyamide and polypropylene spinning masses.

EXAMPLES 22 TO 39

Starting with suitable reagents and following the procedure of Example 1 compounds of the formula

B'—CH=CH—⟨C₆H₄⟩—CH=CH—Q may be produced in which B' and Q are defined in Table 3 below.

TABLE 3

| Ex. No. | B' | Q | melting point | Hue of fluorescence in chlorobenzene |
| --- | --- | --- | --- | --- |
| 22 | C₂H₅O—CO— | coumarinyl-7 | 159–160 | violet-blue |
| 23 | CH₃O—CO— | coumarinyl-7 | 210–212 | violet-blue |
| 24 | C₂H₅O—CO— | 3,4-benzocoumarinyl-7 | 228–229 | violet-blue |
| 25 | CH₃O—CO— | 3,4-benzocoumarinyl-7 | 236–237 | violet-blue |
| 26 | C₂H₅—O—CO— | 4-methylcoumarinyl-7 | 190–192 | reddish-blue |
| 27 | CH₃—O—CO— | 4-methylcoumarinyl-7 | 208–211 | reddish-blue |
| 28 | N≡C— | coumarinyl-7 | 243–244 | reddish-blue |
| 29 | N≡C— | 6-chlorocoumarinyl-7 | 298–301 | blue |
| 30 | N≡C— | 4-methylcoumarinyl-7 | 266–269 | reddish-blue |
| 31 | N≡C— | 3,4-benzocoumarinyl-7 | — | violet-blue |
| 32 | CH₃—O—(CH₂)₂—O—CO— | coumarinyl-7 | 142–143 | violet-blue |
| 33 | CH₃O(CH₂)₂OCO | 3,4-benzocoumarinyl-7 | — | violet-blue |
| 34 | C₂H₅—O—(CH₂)₂—O—CO— | coumarinyl-7 | 127–129 | violet-blue |
| 35 | C₂H₅—O—(CH₂)₂—O—CO— | 3,4-benzocoumarinyl-7 | — | violet-blue |
| 36 | CH₃—(CH₂)₂—O—CO— | coumarinyl-7 | 164–165 | violet-blue |
| 37 | CH₃—(CH₂)₂—O—CO— | 3,4-benzocoumarinyl-7 | — | violet-blue |
| 38 | (CH₃)₂CH—O—CO— | coumarinyl-7 | 174–176 | violet-blue |
| 39 | (CH₃)₂CH—O—CO— | 3,4-benzocoumarinyl-7 | — | violet-blue |

These compounds are useful in particular for use in bath and padding (thermasol) processes for polyester and for a spinning mass of polyester and polyamide.

APPLICATION EXAMPLE A

100 Parts of polyethyleneglycolterephthalate granulate containing 2 parts of titanium dioxide are mixed with 0.02 parts of a compound of formula 5, defined in Example 1. This mixture is melted in a spinning apparatus at 280°–285° whilst stirring and the mass is extruded Alternative to the compound of formula 11, are compounds of formulae 12 or 13

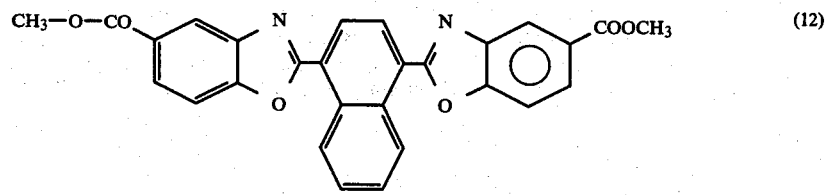

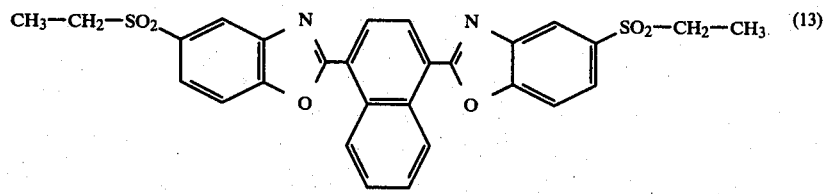

through a spinning nozzle according to known methods. The extruded fibres are cooled, stretched and then wound on spools.

The fibres so produced have a higher whiteness factor than fibres produced according to the same method but without the addition of the optical brightening agent, (the compound of formula 5). Instead of the compound of formula 5 any one of the optical brightening compounds of Examples 2 to 39 may be used to produce an improved whitening effect.

Instead of 0.02 parts of the optical brightener 0.05 parts may be used to improve the whiteness factor without increasing the hue of the brightened fibres.

APPLICATION EXAMPLE B

300 Parts of a polyester granulate containing 6 parts of titanium dioxide are mixed with a fine mixture of equal parts of the compound of formula 5 (defined in Example 1) and 7-naphthotriazolyl-3-phenylcoumarin, a compound of the formula 11

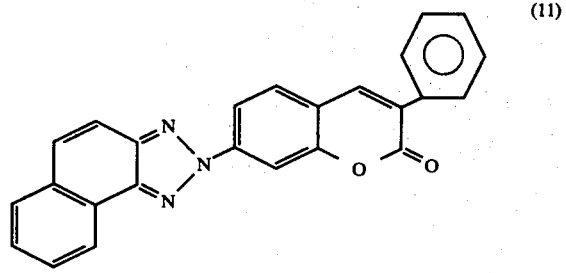

(11)

and the mixture is melted in a spinning apparatus and then spun according to known methods. The stretched and wound fibres have a brilliant white with a violet to neutral hue. The optically brightened fibres have very good light fastness properties. Increasing the amount of optical brigthener present causes the hue of the fibres to become more neutral.

The optical brightener mixture proportions can range for example between 9 parts of a compound of formula 5 to 1 part of a compound of formula 11 to 1 part of a compound of formula 5 to 9 parts of a compound of formula 11. Further, any one of the optical brightening compounds of Example 2 to 39 may be used instead of the compounds of formula 5 in this procedure.

Compounds of the formula (11), (12) and (13) are described in French Patent 1,535,813.

APPLICATION EXAMPLE C

In a high grade steel autoclave 1000 parts of terephthalic acid dimethylester, 800 parts of ethylene glycol, 0.3 parts of a fine mixture of equal parts of the compound of formula 5 (defined in Example 1) and the compound of formula 11 and 1 part of antimony oxide is heated to 200° in a stream of nitrogen and held at this temperature for 3 hours whilst distilling off methanol. The temperature is then raised, over an hour to 280° at which temperature glycol is distilled off. After further heating for 3 hours at 280° under a vacuum of 0.2 torr polycondensation is completed.

The polyester mass can then be spun, the fibres stretched and wound on a spool. The fibres show a brilliant neutral white with good light fastness properties. Any one of the optical brigthening compounds of Examples 2 to 39 can be substituted for the compounds of formula 5 in the above procedure.

APPLICATION EXAMPLE D

A web of polyester fibres is printed with an aqueous dispersion containing per liter 1 g of the compound of Example 22, 0.1 g of a dispersing agent derived from dinaphthylmethane disulphonic acid. The material is then dried at about 100°. Finally for a short time the material is heated to 220°. The so treated web shows a brilliant, neutral blue optical brightening effect with good light fastness properties. Instead of the compound of Example 22 any one of the optical brightening compounds of Examples 1 to 21 and 23 to 39 may be used to provide similar effects.

APPLICATION EXAMPLE E

A web of polyester fibres is treated in a bath of liquor to goods ratio 40:1, containing 0.2% of the optical brightener of Example 10 in the form of an aqueous dispersion (produced with the aid of a dispersing agent derived from dinaphthylmethanedisulphonic acid in a sand grinder) for 30 minutes at the boil. The web when so treated has a brilliant neutral white tone. In a similar fashion the optical brightening compounds of Examples 1 to 9 and 11 to 39 can produce similar effects.

The whitening effect can be improved by carrying the process out in a closed apparatus at 130° C. instead of 98° C. (boiling) or by carrying the process out at 98°

C. (boiling) with the addition of 2 g/l trichlorobenzene. In a similar bath to the above, instead of treating a polyester web a polyamide web may be so treated. Suitable polyamide webs are those made of Nylon 6 or Nylon 66 or a web of cellulose 2,5-diacetate. The bath however is raised to 70° rather than to the boil and the treated polyamide web shows an improved whitening with a reddish to neutral blue hue.

What is claimed is:

1. A compound of the formula I'

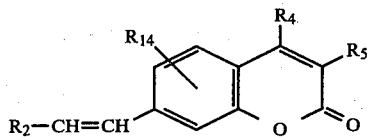

where $R_2$ is one of the groups (ii), (iii) and (iv)

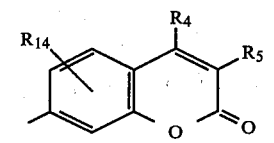 (ii)

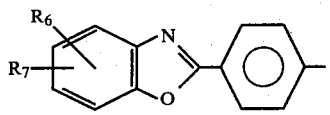 (iii)

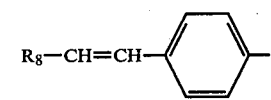 (iv)

$R_4$ and $R_5$, independently are hydrogen, $C_{1-4}$alkyl or $C_{1-4}$alkyl monosubstituted by phenyl which phenyl is unsubstituted or monosubstituted by methoxy, methyl or chlorine; or $R_4$ and $R_5$ together with the coumarinyl-7 group to which they are attached form a 3,4-benzocoumarinyl-7 in which the 3,4-benzo group is substituted by two substituents $R_{20}$ selected from hydrogen, $C_{1-4}$alkyl, $C_{1-4}$alkoxy or chlorine or $R_4$ and $R_5$ together with the coumarinyl-7 group to which they are attached form a 3,4-fused cyclo $C_{5-6}$alkenyl coumarinyl-7 group which is substituted by two groups $R_{20}$ defined above, the pairs $R_4$ and $R_5$ shown in formulae I' and (ii), respectively, being the same or different, either $R_6$ and $R_7$ independently are hydrogen, $C_{1-4}$-alkyl, halogen or $C_{1-4}$alkyl substituted by a phenyl group which is unsubstituted or monosubstituted by methyl, methoxy or chlorine;

or $R_6$ and $R_7$ together form a —CH$_2$CH$_2$CH$_2$— or —CH$_2$CH$_2$CH$_2$CH$_2$— group which is attached to adjacent carbon atoms of the phenyl ring;

$R_8$ is —CN, —COOR$_9$, CONR$_{10}$R$_{11}$ or SO$_2$R$_{12}$;

$R_9$ and $R_{12}$ independently are $C_{1-4}$alkyl, $C_{1-4}$alkyl substituted by a phenyl group which is unsubstituted or monosubstituted by methyl, methoxy or chloro, $C_{2-4}$alkyl monosubstituted by hydroxy, $C_{1-4}$alkoxy or $C_{1-4}$alkoxy-$C_{2-6}$alkoxy, cyclohexyl unsubstituted or substituted by up to three methyl groups or phenyl unsubstituted or monosubstituted by $C_{1-4}$alkyl, trifluoromethyl, cyano, $C_{1-4}$alkoxy, chloro or carboxy;

$R_{10}$ is hydrogen, $C_{1-4}$alkyl, $C_{1-4}$alkyl substituted by phenyl which is unsubstituted or monosubstituted by methyl, methoxy or chloro, or $C_{2-4}$alkyl monosubstituted by hydroxy, $C_{1-4}$-alkoxy or $C_{1-4}$alkoxy-$C_{2-6}$alkoxy; and $R_{11}$ has the significances of $R_{10}$ (independently of $R_{10}$) and phenyl unsubstituted or substituted by $C_{1-4}$alkyl, trifluoromethyl, chloro, cyano, carboxy or $C_{1-4}$alkoxy;

$R_{14}$ is hydrogen, chlorine, $C_{1-4}$alkyl or $C_{1-4}$alkyl substituted by phenyl, which phenyl is unsubstituted or monosubstituted by methoxy, methyl or chloro.

2. A compound according to claim 1 of the formula II

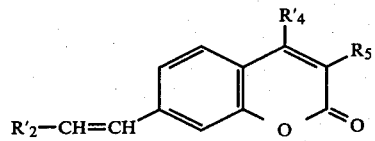

in which $R_2'$ is one of the groups (ii), (iii) and (iv) defined in claim 1, where in group (ii) $R_4$ and $R_5$ have the significance of $R_4'$ and $R_5$ defined below, where in group (iii) $R_6$ is $R_6'$ and $R_7$ is hydrogen and where in group (iv) $R_8$ is defined in claim 1;

$R_4'$ is hydrogen, methyl, ethyl, isopropyl, isobutyl or tertiary butyl and $R_5$ is hydrogen or $R_4'$ and $R_5$ together with the coumarinyl-7 group to which they are attached form a 3,4-benzocoumarinyl-7 group substituted by up to two $R_{20}$ groups $R_{20}$ being defined in claim 1;

$R_6'$ is hydrogen, chloro, methyl, ethyl, isopropyl, isobutyl or tertiary butyl.

3. A compound according to claim 2 of the formula III

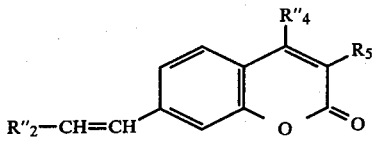

where $R_2''$ is selected from one of the groups (iia), (iiia) or (iva)

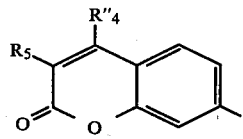 (iia)

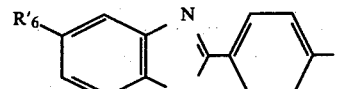 (iiia)

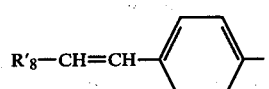 (iva)

in which
$R_4''$ is hydrogen or methyl and $R_5$ is hydrogen or $R_4''$ and $R_5$ together with the coumarinyl-7 group to which they are attached form a 3,4-benzocoumarinyl-7 group in which the 3,4-benzo group is substituted by two groups $R_{20}'$ where $R_{20}'$ is hydrogen, methyl, ethyl, isopropyl, isobutyl or tertiary butyl, $R_8'$ is —CN or —COOR$_9'$ where $R_9'$ is $C_{1-4}$alkyl or $C_{2-3}$alkyl monosubstituted by methoxy or ethoxy.

4. A compound according to claim 3 of the formulae IIIa or IIIb

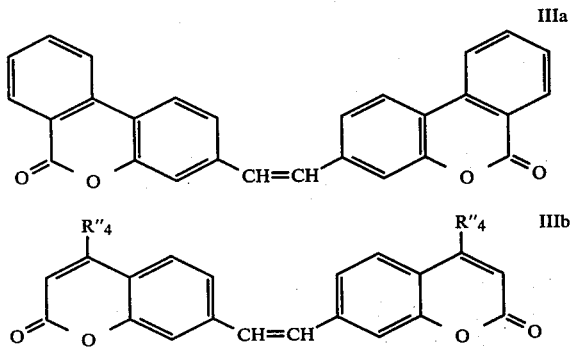

in which $R_4''$ is hydrogen or methyl.

5. A compound according to claim 1 wherein $R_4$ and $R_5$, independently, are hydrogen or $C_{1-4}$alkyl or together with the coumarinyl-7 group to which they are attached form a 3,4-benzocoumarinyl-7 group in which the 3,4-benzo group is substituted by up to two $R_{20}$ substituents;

$R_{14}$ is hydrogen or chlorine; and $R_{20}$ is hydrogen or $C_{1-4}$alkyl.

6. A compound according to claim 5 wherein $R_4$ is hydrogen, methyl, ethyl, isopropyl, isobutyl or tertiary butyl and $R_5$ is hydrogen or $R_4$ and $R_5$ together with the coumarinyl-7 group to which they are attached form a 3,4-benzocoumarinyl-7 group in which the 3,4-benzo group is substituted by up to two substituents $R_{20}'$; and $R_{20}$ is $R_{20}'$ which is selected from hydrogen, methyl, ethyl, isopropyl, isobutyl and tertiary butyl.

7. A compound according to claim 1 or 5 wherein $R_6$ is hydrogen, chloro, or $C_{1-4}$alkyl, $R_7$ is hydrogen, $R_8$ is —CN or —COOR$_9$, and $R_9'$ is $C_{1-4}$alkyl or $C_{2-3}$alkyl monosubstituted by methoxy or ethoxy.

8. A compound according to claims 1, 2, 3, 5 or 6 which is symmetrical.

9. A compound according to claim 7 which is symmetrical.

* * * * *